(12) United States Patent
Smith et al.

(10) Patent No.: US 11,141,161 B2
(45) Date of Patent: Oct. 12, 2021

(54) FULL EVERSION ANASTOMOSIS JUNCTURE FORMATION AND SUTURING

(71) Applicant: Spiration, Inc., Redmond, WA (US)

(72) Inventors: Adam Lee Smith, Palm Desert, CA (US); Clifton A. Alferness, Olalla, WA (US); Gina M. Muia-Longman, Seattle, WA (US); Clinton L. Finger, Bellevue, WA (US)

(73) Assignee: Gyrus ACMI, Inc., Westborough, MA (US)

( * ) Notice: Subject to any disclaimer, the term of this patent is extended or adjusted under 35 U.S.C. 154(b) by 338 days.

(21) Appl. No.: 16/367,158

(22) Filed: Mar. 27, 2019

(65) Prior Publication Data

US 2019/0343529 A1 Nov. 14, 2019

Related U.S. Application Data

(60) Provisional application No. 62/676,452, filed on May 25, 2018, provisional application No. 62/668,696, filed on May 8, 2018.

(51) Int. Cl.
*A61B 17/115* (2006.01)
*A61B 90/00* (2016.01)
(Continued)

(52) U.S. Cl.
CPC ...... *A61B 17/1152* (2013.01); *A61B 17/0469* (2013.01); *A61B 17/11* (2013.01);
(Continued)

(58) Field of Classification Search
CPC . A61B 17/1152; A61B 17/11; A61B 17/0469; A61B 17/0482; A61B 17/06066;
(Continued)

(56) References Cited

U.S. PATENT DOCUMENTS 6,514,263 B1 2/2003 Stefanchik et al.
6,530,932 B1 3/2003 Swayze et al.
(Continued)

OTHER PUBLICATIONS

Assessment of Patented Coronary End-to-Side Anastomotic Devices Using Micromechanical Bonding.

*Primary Examiner* — Erich G Herbermann
*Assistant Examiner* — Chima U Igboko
(74) *Attorney, Agent, or Firm* — Clements Bernard Walker; Frank J. Bozzo

(57) ABSTRACT

Disclosed embodiments include apparatuses, systems, and methods for facilitating anastomosis between bodily passages. In an illustrative embodiment, an eversion mechanism is configured to engage a first external surface of a receiving passage adjacent a first opening in the receiving passage in order to create a receiving flange presenting a first interior face. A donor support mechanism is configured to support a donor passage with an opening in an end in an everted position that forms a donor flange presenting a second interior face. The donor support mechanism is further configured to present the second interior face of the donor flange against the first interior face of the receiving flange to present a passage juncture. A suturing mechanism is configured to motivate a filament through a helical path around the passage juncture to suture the second interior face of the donor passage to the first interior face of the receiving passage.

10 Claims, 12 Drawing Sheets

(51) Int. Cl.
*A61B 17/04* (2006.01)
*A61B 17/11* (2006.01)
*A61B 17/00* (2006.01)

(52) U.S. Cl.
CPC ............ *A61B 90/361* (2016.02); *A61B 90/37* (2016.02); *A61B 2017/00566* (2013.01); *A61B 2017/1107* (2013.01); *A61B 2017/1121* (2013.01); *A61B 2017/1125* (2013.01); *A61B 2017/1132* (2013.01)

(58) Field of Classification Search
CPC . A61B 17/02; A61B 17/1114; A61B 17/1128; A61B 17/1146; A61B 17/115; A61B 17/1155; A61B 2017/00566; A61B 2017/1107; A61B 2017/1132; A61B 2017/1125; A61B 2017/1121; A61B 2017/306; A61B 2017/06076; A61B 2017/00252; A61B 2017/1135; A61B 2017/0243; A61B 2017/1103; A61B 2017/111; A61B 2017/1117; A61B 2017/1139; A61B 2017/1142; A61B 2017/1157; A61B 90/361; A61B 90/37
See application file for complete search history.

(56) References Cited

U.S. PATENT DOCUMENTS

| | | |
|---|---|---|
| 6,613,058 B1 | 9/2003 | Goldin |
| 2006/0030869 A1* | 2/2006 | Loshakove ...... A61B 17/00491 606/153 |
| 2007/0233188 A1* | 10/2007 | Hunt ................. A61B 17/0487 606/228 |
| 2012/0143226 A1* | 6/2012 | Belson ............... A61B 17/0057 606/148 |

* cited by examiner

FULL EVERSION ANASTOMOSIS JUNCTURE FORMATION AND SUTURING

PRIORITY CLAIM

The present application claims the priority and benefit of U.S. Provisional Patent Application Ser. No. 62/668,696 for "SYSTEMS AND METHODS FOR PERFORMING CORONARY ARTERY BYPASS GRAFTING" filed May 8, 2018, and U.S. Provisional Patent Application Ser. No. 62/676,452 for "SYSTEMS AND METHODS FOR PERFORMING CORONARY ARTERY BYPASS GRAFTING" filed May 25, 2018.

FIELD

The present disclosure relates to apparatuses, systems, and methods for presenting and joining an opening in an end of a donor passage to an opening in a receiving passage.

BACKGROUND

The statements in this section merely provide background information related to the present disclosure and may not constitute prior art.

Surgical anastomosis enables segments of one or more arteries, blood vessel, intestines, or any other passages to be connected or reconnected, such as in coronary artery bypass graft (CABG) procedures. In a CABG procedure, for example, a saphenous vein may be harvested from a patient's leg and grafted to circumvent coronary arterial blockages. Such procedures are tremendously useful and may regularly save and extend lives.

However, CABG procedures and similar procedures involve highly invasive surgery. For example, a typical CABG procedure involves performing a median sternotomy in which a vertical incision is made along the patient's sternum, after which the sternum itself is actually broken open to provide access to the heart and surrounding arteries. The median sternotomy provides a surgeon with space to insert a graft and suture the graft to a coronary artery to complete the process. However, the sizable incision and the breaking of the sternum may involve significant scarring, discomfort, and risk of infection, and may require significant recovery time for the healing of the affected structures.

SUMMARY

Disclosed embodiments include apparatuses, systems, and methods for facilitating surgical anastomosis between bodily passages, such as veins and arteries or other passages.

In an illustrative embodiment, an apparatus includes an eversion mechanism configured to engage a first external surface of a receiving passage adjacent a first opening in the receiving passage in order to create a receiving flange that presents a first interior face. A donor support mechanism is configured to support a donor passage with an opening in an end in an everted position that forms a donor flange that presents a second interior face. The donor support mechanism is further configured to present the second interior face of the donor flange against the first interior face of the receiving flange to present a passage juncture. A suturing mechanism is configured to motivate a filament through a helical path around the passage juncture to suture the second interior face of the donor passage to the first interior face of the receiving passage.

In another illustrative embodiment, a system includes a support body configured to be inserted into a body. A camera system is operably coupled with the support body, wherein the camera system is enabled to convey imaging data from the support body to an operator. An eversion mechanism extends from the support body and is configured to engage a first external surface of a receiving passage adjacent a first opening in the receiving passage in order to create a receiving flange that presents a first interior face. A donor support mechanism extends from the support body and is configured to support a donor passage with an opening in an end in an everted position that forms a donor flange that presents a second interior face. The donor support mechanism is configured to present the second interior face of the donor flange against the first interior face of the receiving flange to present a passage juncture. A suturing mechanism is configured to motivate a filament through a helical path around the passage juncture to suture the second interior face of the donor passage to the first interior face of the receiving passage.

In a further illustrative embodiment, a method includes, at a first opening in a side of a receiving passage, everting a first edge of the first opening around a periphery of the first opening to form a receiving flange that presents a first interior face. A donor passage is provided, where the donor passage has an opening in an end that terminates in a second opening. A second edge of the second opening is everted to form a donor flange that presents a second interior face. The second interior face of the donor passage is positioned adjacent the first interior face of the receiving passage to form a passage juncture. A filament is motivated along a helical path around the passage juncture to suture the second interior face of the donor passage to the first interior face of the receiving passage.

Further features, advantages, and areas of applicability will become apparent from the description provided herein. It will be appreciated that the description and specific examples are intended for purposes of illustration only and are not intended to limit the scope of the present disclosure.

DRAWINGS

The drawings described herein are for illustration purposes only and are not intended to limit the scope of the present disclosure in any way. The components in the figures are not necessarily to scale, with emphasis instead being placed upon illustrating the principles of the disclosed embodiments. In the drawings.

Figure 1:
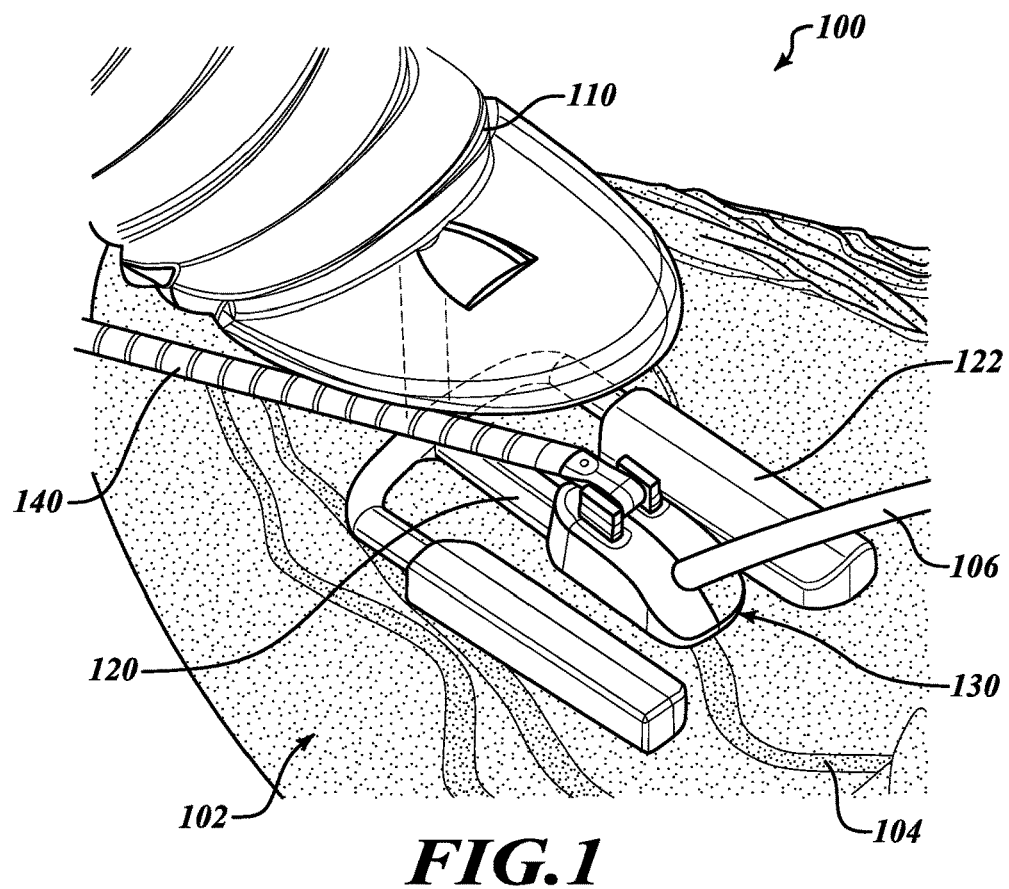
FIG. 1 is a schematic diagram of an illustrative system positioned on a heart for performing an illustrative CABG procedure.
Figure 2:
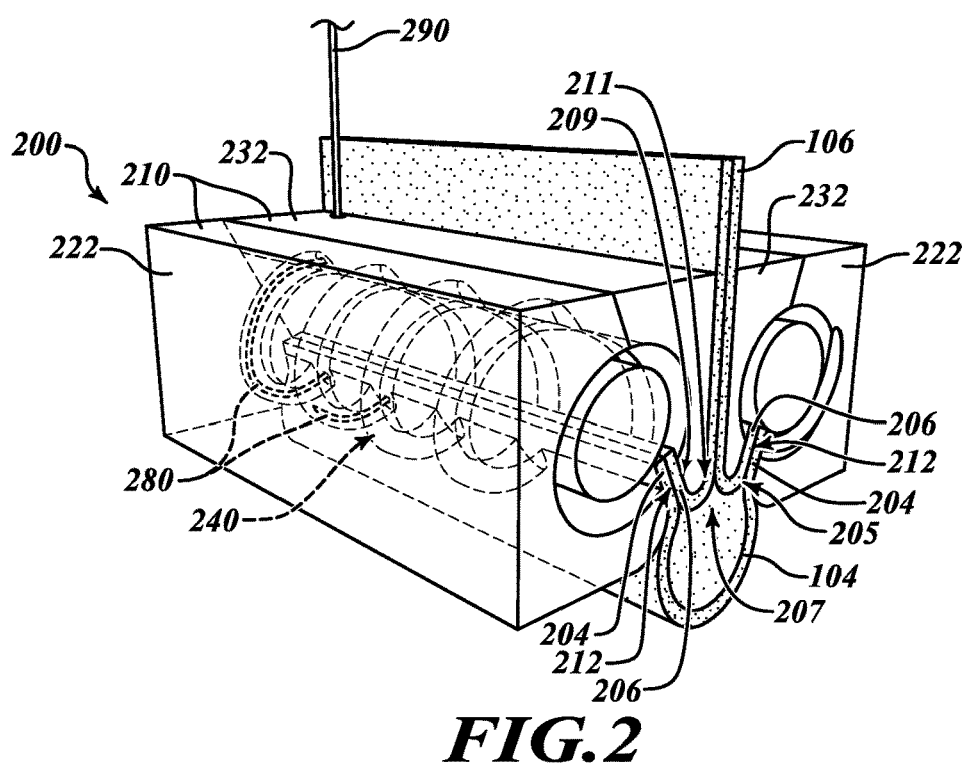
FIG. 2 is a perspective view in partial cutaway form of a suturing mechanism disposed to suture a passage juncture formed by a donor flange positioned against a receiving flange.
Figure 5A:
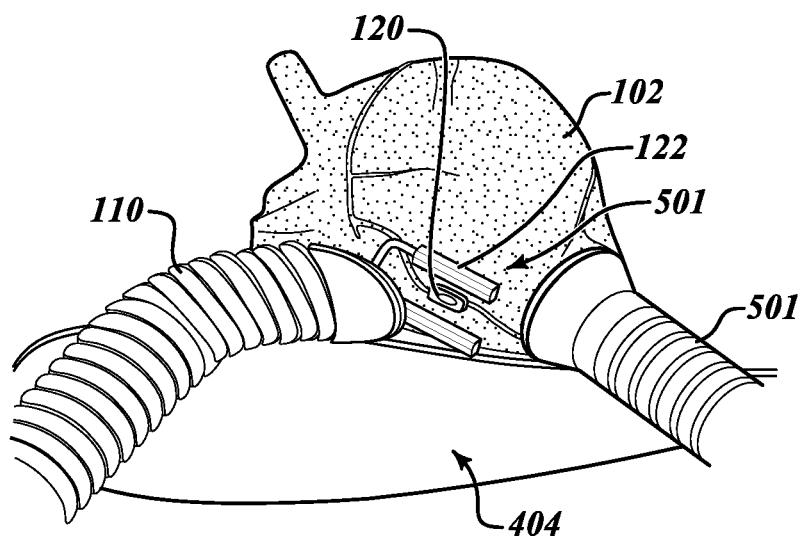
Figure 5B:
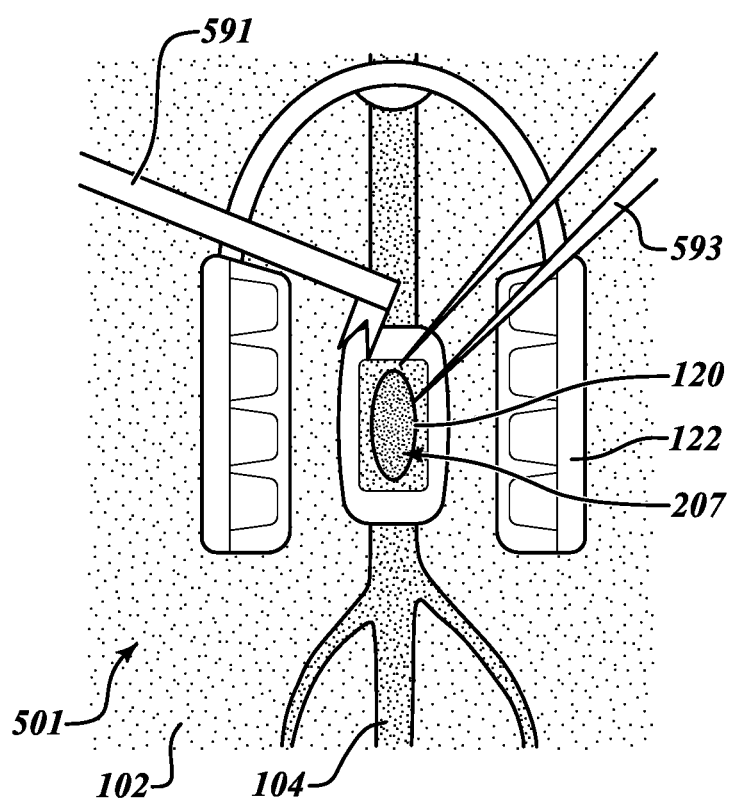
Figure 6A:
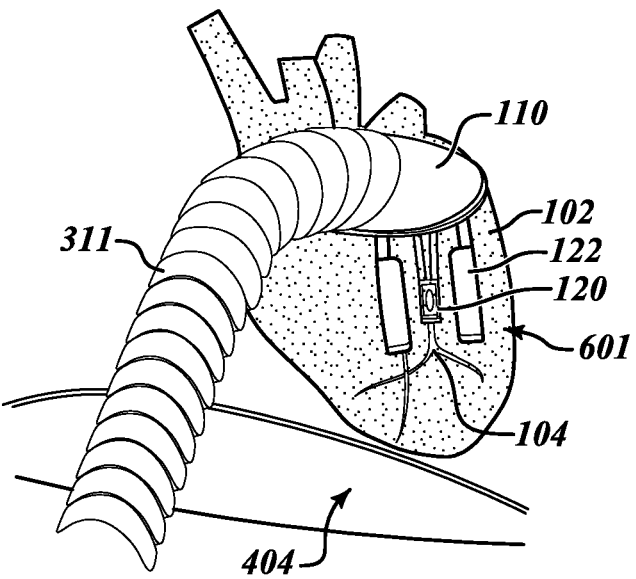
Figure 6B:
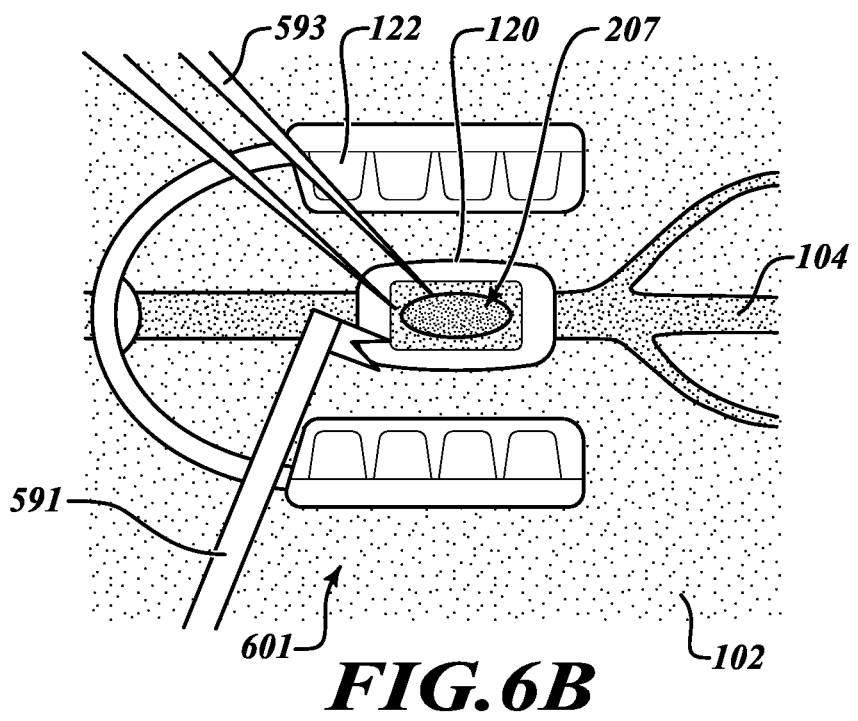
Figure 7A:
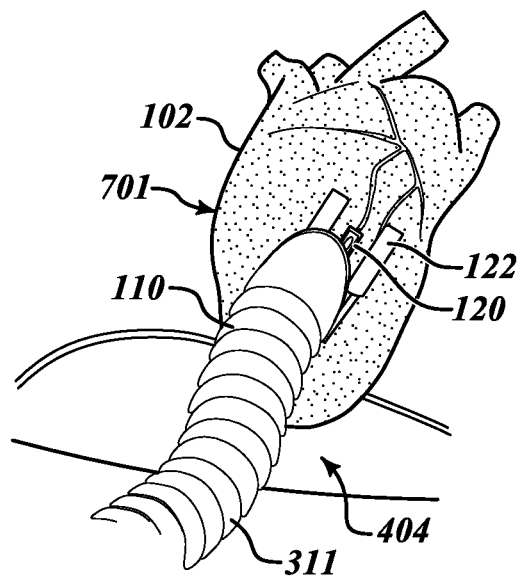
Figure 7B:
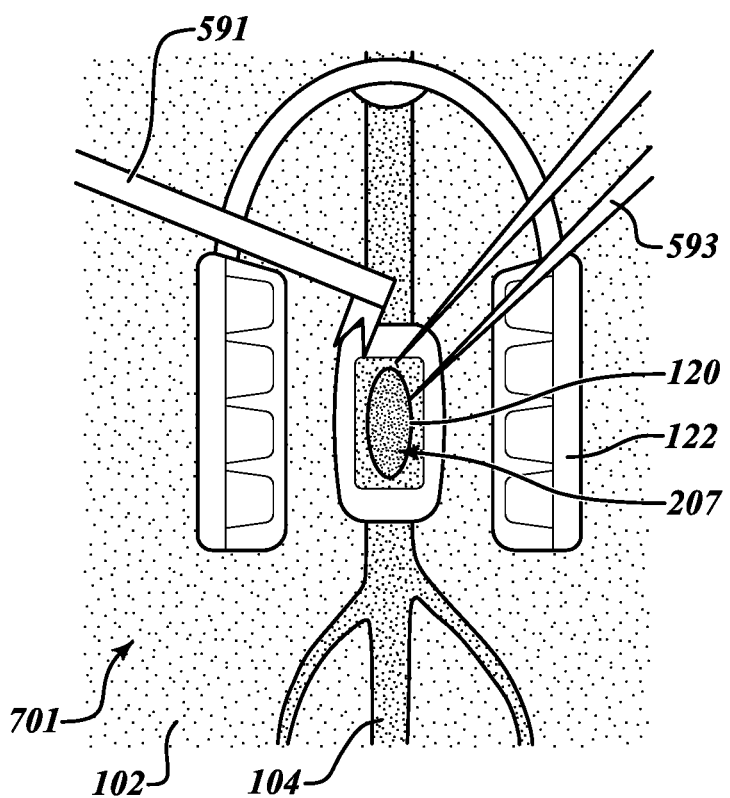
Figure 8:
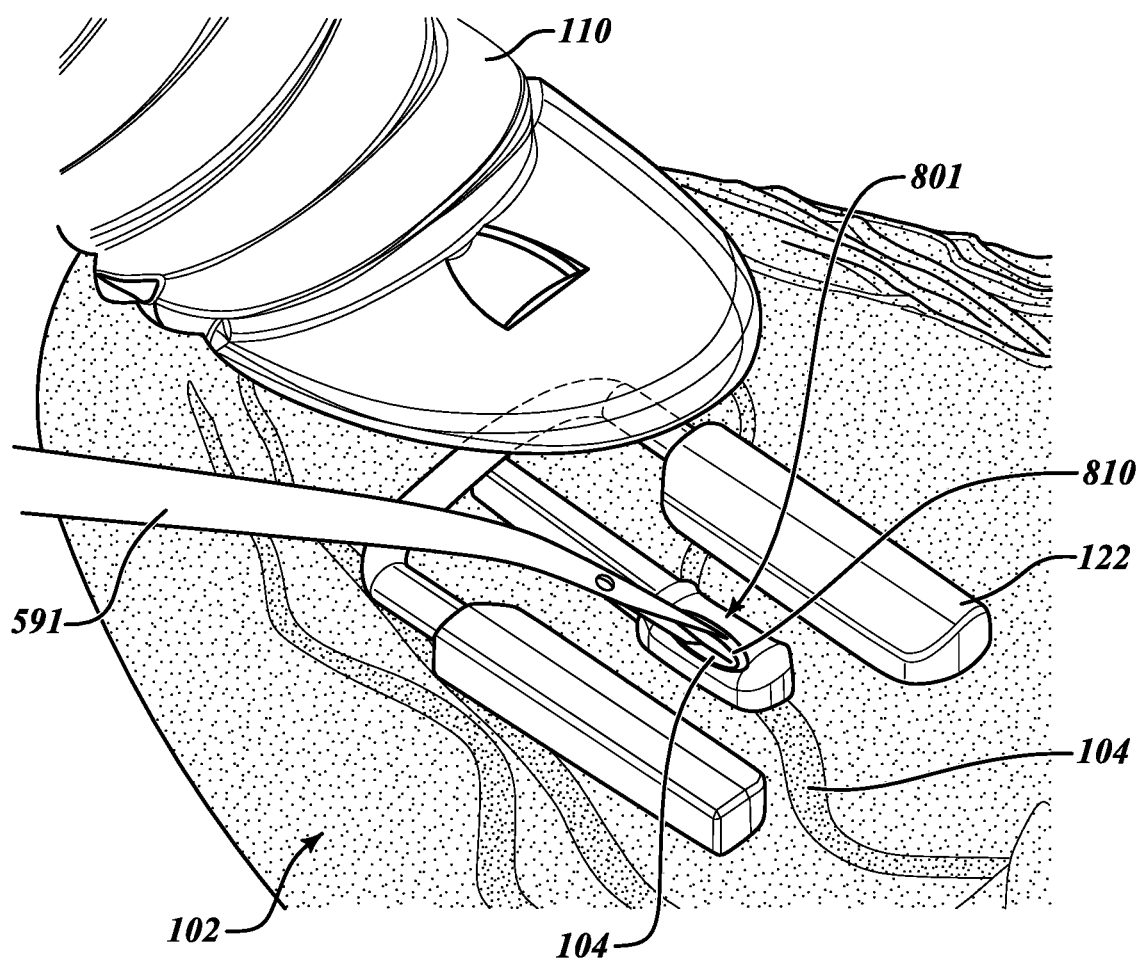
Figure 9A:
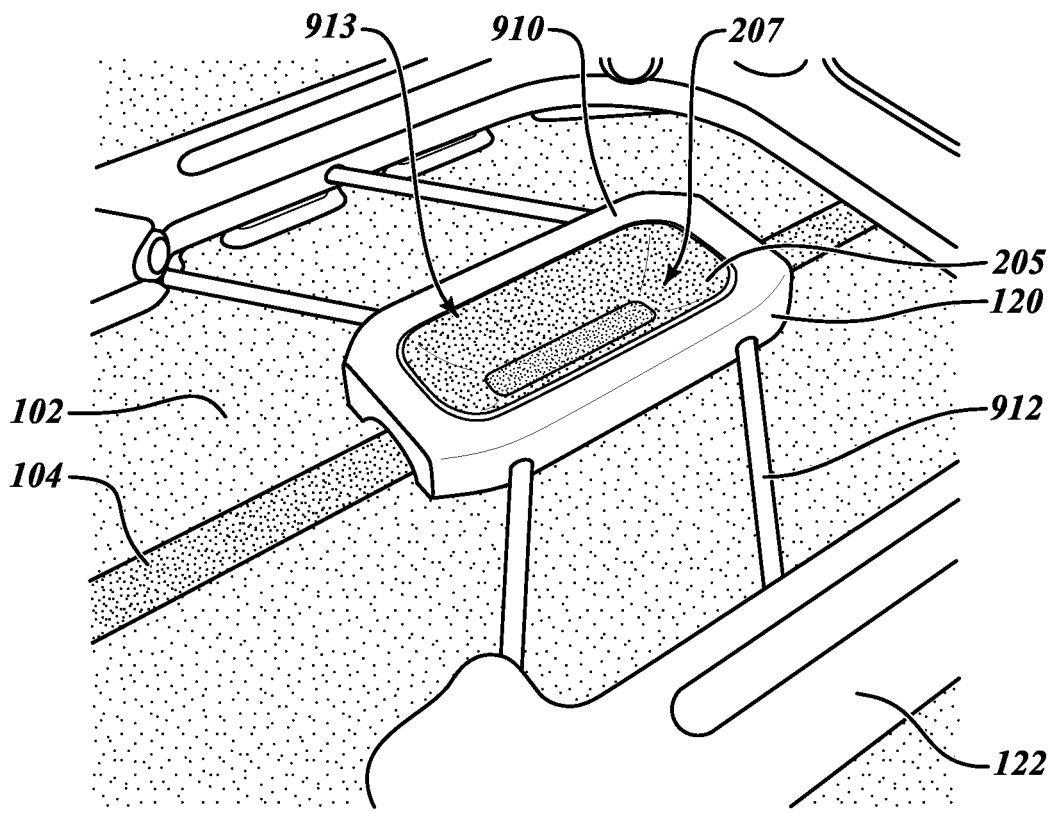
Figure 9B:
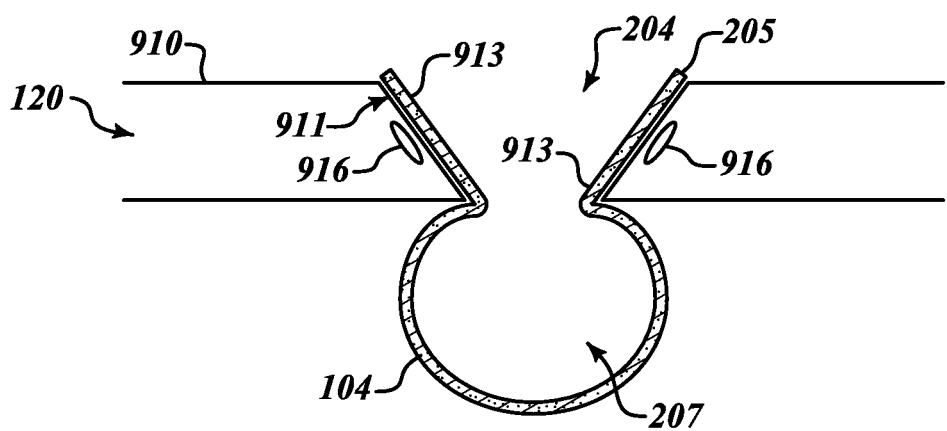
Figure 10A:
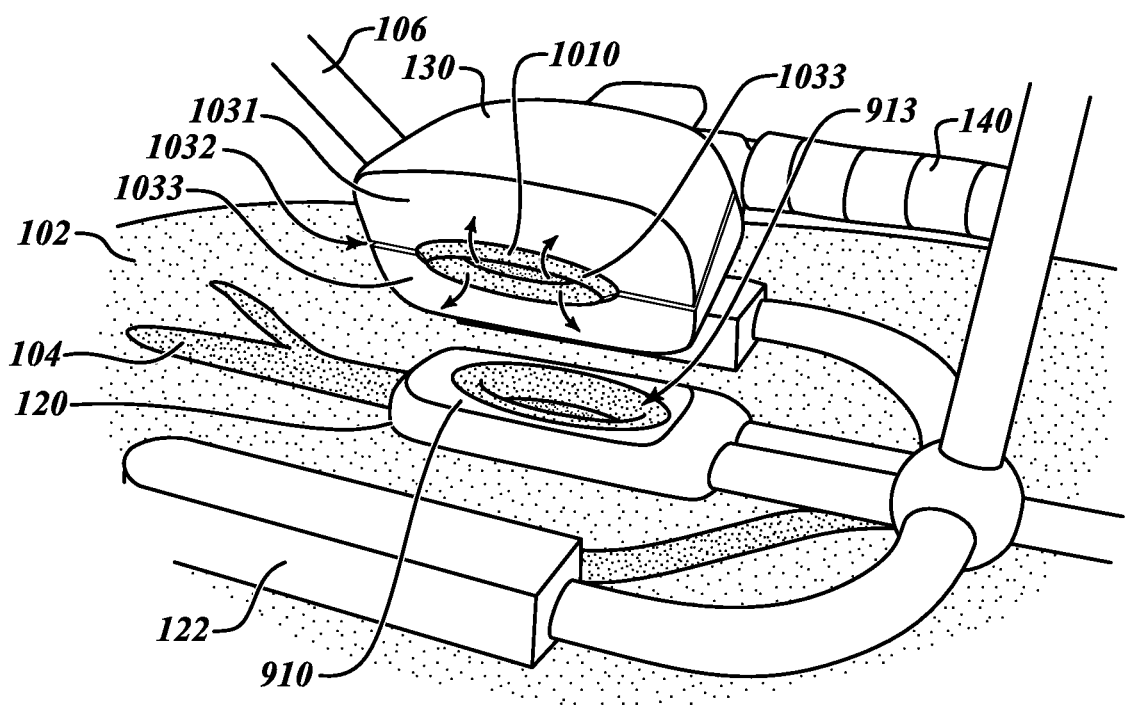
Figure 10B:
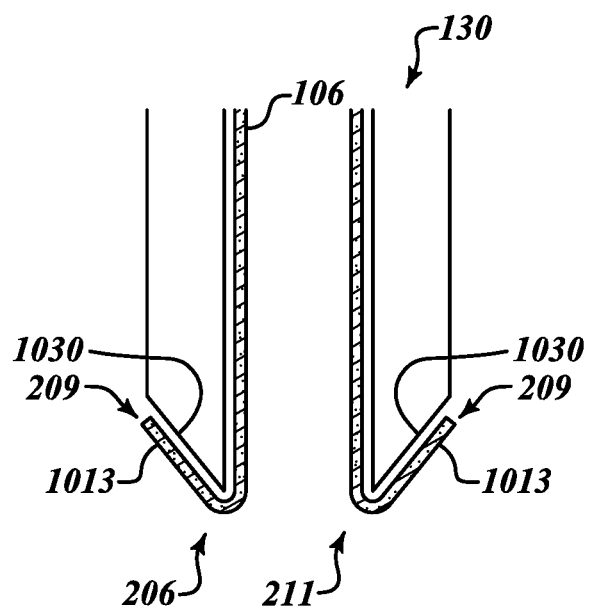
Figure 11A:
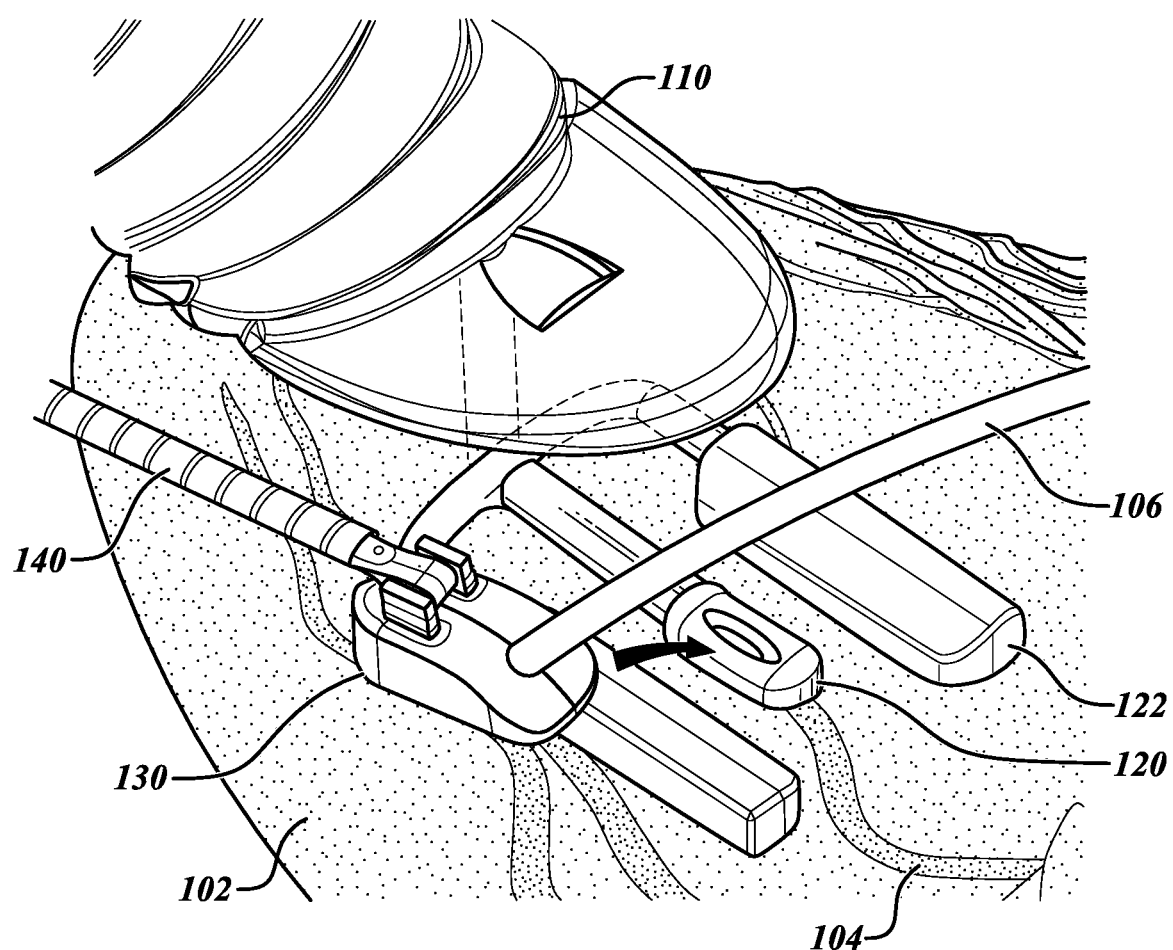
Figure 11B:
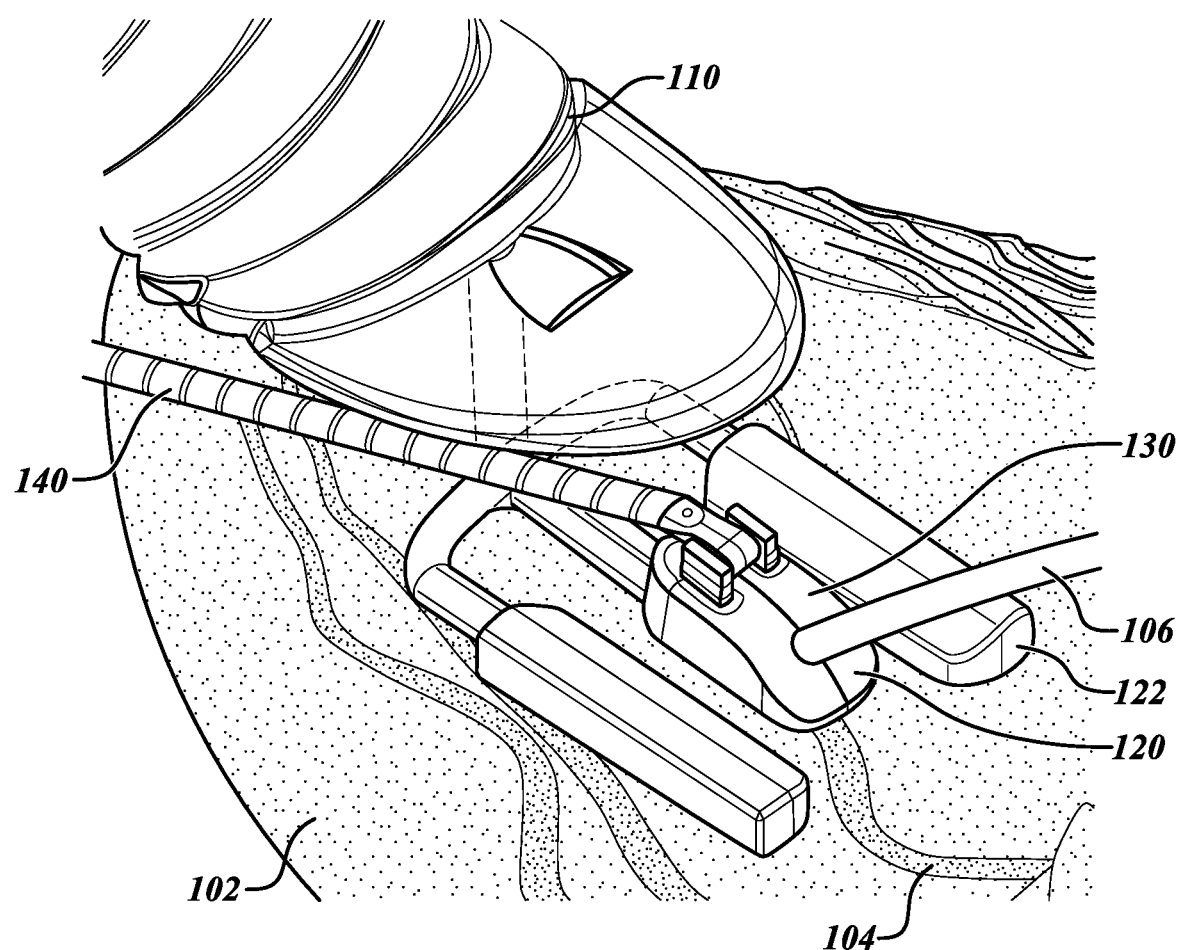
Figure 12:
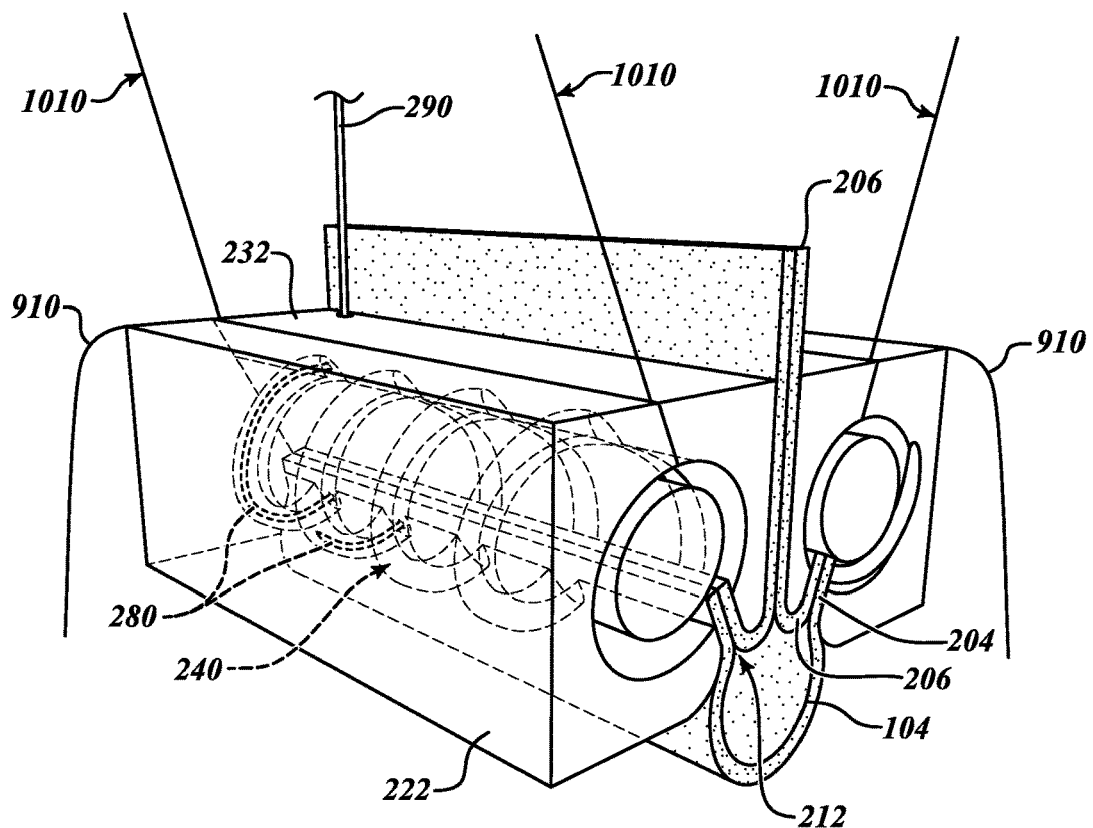
Figure 13A:
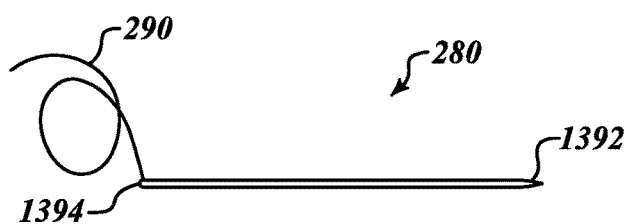
Figure 13B:
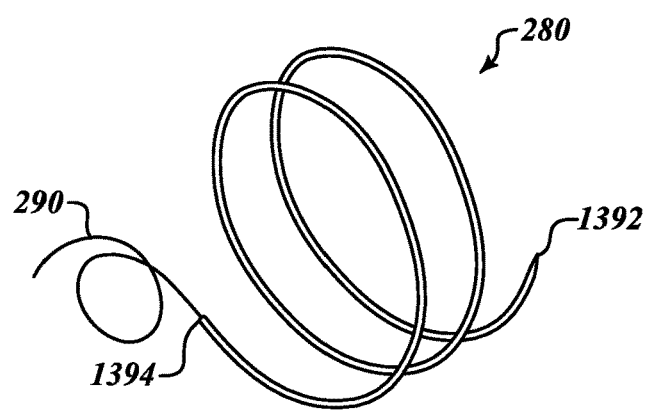
Figure 14:
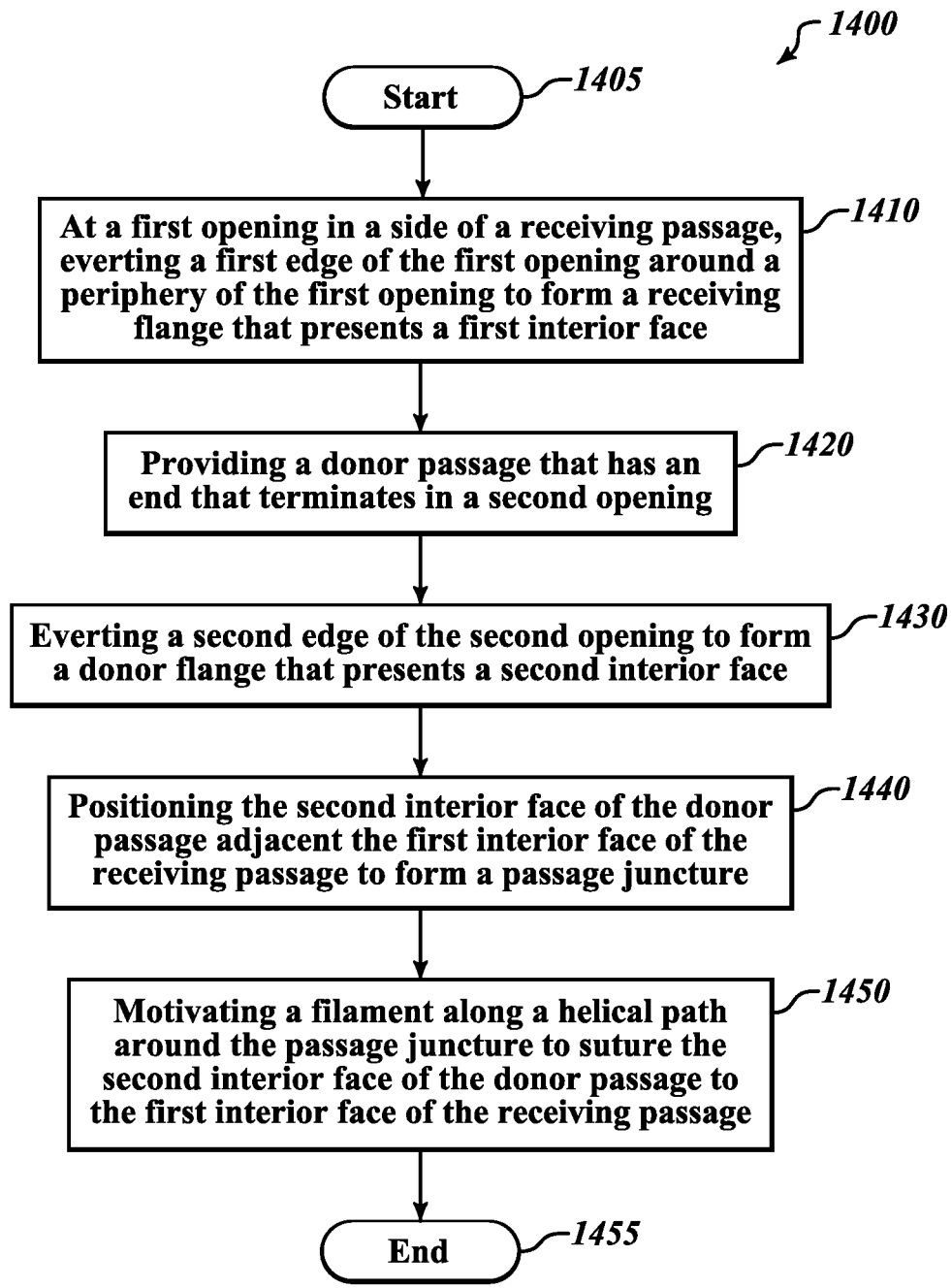

FIGS. 5A, 6A, and 7A are perspective views of the system of FIG. 1 disposed in various orientations on a heart;

FIGS. 5B, 6B, and 7B are perspective view of an eversion mechanism of the system of FIG. 1 as disposed on a heart corresponding to the perspective views of FIGS. 5A, 6A, and 7A, respectively;

FIG. 8 is a schematic diagram of the system of FIG. 1 prior to everting a first opening in a receiving passage;

FIG. 9A is a schematic diagram of an eversion mechanism of the system of FIG. 1 used to evert the first opening in the receiving passage;

FIG. 9B is a cross-sectional view of the eversion mechanism and the everted first opening;

FIG. 10A is a schematic diagram of an eversion mechanism of the system of FIG. 1 used to evert an end of the donor passage;

FIG. 10B is a cross-sectional view of the everted end of the donor passage;

FIG. 11A is a schematic diagram of the eversion support mechanism showing the donor passage being positioned against the everted first opening in the receiving passage;

FIG. 11B is a schematic diagram of the everted end of the donor passage positioned against the first opening in the receiving passage forming a passage juncture;

FIG. 12 is a perspective view of the suturing mechanism of FIG. 2 integrated into the system of FIG. 1 in partial cross-section for guiding a needle to suture the passage juncture;

FIGS. 13A and 13B are perspective views of needles that may be used in conjunction with the suturing mechanism to suture the passage junction; and FIG. 14 is a flow diagram of an illustrative method of performing an anastomosis procedure according to the present disclosure.

DETAILED DESCRIPTION

The following description is merely illustrative in nature and is not intended to limit the present disclosure, application, or uses. It will be noted that the first digit of three-digit reference numbers, the first two digits of four-digit reference numbers correspond to the first digit of one-digit figure numbers and the first two-digits of the figure numbers, respectively, in which the element first appears.

The following description explains, by way of illustration only and not of limitation, various embodiments of noninvasive apparatuses, systems, and methods for positioning a receiving passage and a donor passage, and suturing the passages together in a surgical anastomosis procedure. The apparatuses, systems, and methods are described using the example of a CABG procedure involving the joining of a saphenous vein to a coronary artery in a CABG procedure. However, it will be appreciated that the same methods, apparatuses, and systems may be used for other grafting or anastomosis procedures for other arteries, intestines, or other bodily passages.

Referring to FIG. 1, a system 100 is positioned on a patient's heart 102 at a receiving passage 104. In a nonlimiting example given by way of illustration only and not of limitation, in various embodiments the receiving passage 104 is a coronary artery that may be involved in a CABG procedure. The system 100 includes a support body 110 that is configured to physically support and guide other components in a noninvasive anastomosis procedure, as further described below. The system 100 also includes an eversion mechanism 120 that is configured to engage and manipulate a side of the receiving passage 104 that will become the receiving passage in the CABG procedure, as further described below. The eversion mechanism 120 may include a stabilizer 122 to secure a position of the heart 102 and maintain a position of the eversion mechanism 120 and the rest of the system 100 relative to the heart 102. The system 100 also includes a donor support mechanism 130 configured to support a donor passage 106. In the example used by this description, the donor passage 106 is a saphenous vein that may be involved in a CABG procedure. The donor support mechanism 130 is used to move the donor passage 106 into position relative to the receiving passage 104 for grafting. A suturing mechanism (not shown in FIG. 1) operably coupled with the eversion mechanism 120 and the donor support mechanism 130 is used to suture the donor passage 106 to the receiving passage 104, as also described further below with reference to FIG. 2 and other figures. In an illustrative embodiment, a control conduit 140 is coupled with the donor support mechanism 130 for performing the suturing to complete the graft, as described below.

As previously stated, although this description will use the example of a CABG procedure, it will be appreciated that the same apparatuses, systems, and methods may be used for other anastomosis procedures. Accordingly, in the interest of simplicity, the following description refers only to the example of the donor passage 106 being grafted to the receiving passage 104, although similar procedures may be performed with other donor passages and receiving passages.

Referring to FIG. 2, in various embodiments a suturing mechanism 200 includes one or more sets of opposing guide sections 210 that are disposed around a passage juncture 212 formed by surfaces of the receiving passage 104 and the donor passage 106. More specifically, the passage juncture 212 is formed in part by a receiving flange 204 that is formed by everting an edge 205 of an opening 207 formed in the receiving passage 104, as described below with reference to FIGS. 8, 9A, and 9B. The passage juncture 212 is also formed by a donor flange 206 that is formed by everting an edge 209 of an opening in an end 211 of the donor passage 106, as described below with reference to FIGS. 10A and 10B. The one or more sets of opposing guide sections 210 are shaped to accommodate the receiving flange 204 and the donor flange 206 of the passage juncture 212. A receiving guide section 222 is configured to engage an outer side of the receiving flange 204 and a donor guide section 232 is configured to engage an outer side of the donor flange 206. Inner faces of each of the sets of opposing guide sections 210 are shaped to define a helical channel 240 that will direct a flexible needle 280 to lead a suture 290 in suturing the passage juncture 212, as further described below. Although not shown in FIG. 2, the receiving guide section 222 may be one of joined to or formed integrally with the eversion mechanism 120, and the donor guide section 232 may be one of joined to or formed integrally with the donor support mechanism 130.

Figure 3:
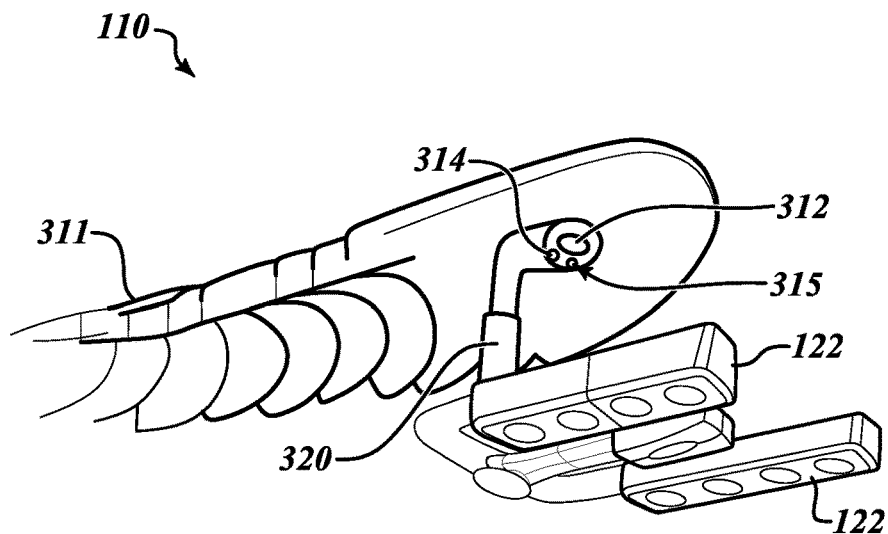
FIG. 3 is a schematic diagram of the system of FIG. 1 shown from an underside prior to being positioned on the heart.

Referring to FIG. 3, in various embodiments an underside of the support body 110 supports the eversion mechanism 120 and the stabilizer 122. The eversion mechanism 120 and the stabilizer 122 may be coupled to the support body 110 with a bracket 320. The support body 110 includes a handle 311 that enables an operator (not shown in FIG. 3) to insert the support body 110 through an opening such as may be formed by an incision, as further described below with reference to FIG. 4. After inserting the support body 110 into the opening, the operator can then manipulate the handle 311 to position the support body 110 and, thus, the attached eversion mechanism 120 and stabilizer 122, and to withdraw the same after the procedure is completed. The handle 311 also may convey through the support body 110 and the bracket 320 tubing and/or wiring to control operation of the eversion mechanism, as described further below.

The support body 110 also may include other components to assist the operator in performing the procedure. In various embodiments, the support body 110 may include an optical system 315 to aid the operator in guiding the support body 110 to a desired location and completing the procedure. The optical system 315 may include a camera 312 to provide imaging data, via a wired or a wireless connection, to a display that may be viewed by the operator. The optical system 315 also may include a light source 314 to provide illumination in the vicinity of the support body to facilitate capturing useful optical imaging data with the camera 312.

Figure 4:
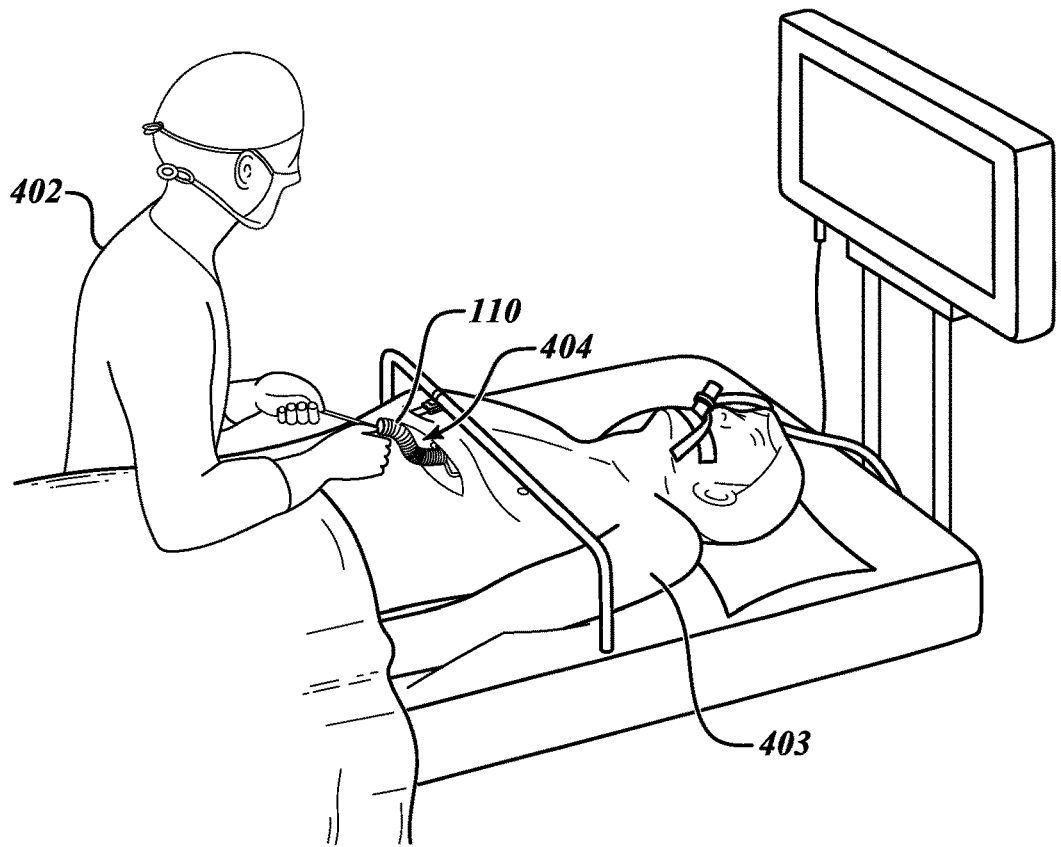
FIG. 4 is a schematic diagram showing insertion of the system of FIG. 1 into a patient for performance of the CABG procedure.

Referring to FIG. 4, in various embodiments an operator 402 deploys the support body 110 (and its associated components) to perform a procedure on a patient 403. In the example of a CABG procedure, the support body 110 may be deployed through a subxiphoid incision 404 made below the sternum of the patient 403. Using the system 100 and manipulating the support body 110 and its associated components, the operator 402 may be able to perform a procedure on the patient 403 with minimal invasiveness. For example, in the case of a CABG procedure, a conventional procedure would involve a median sternotomy with one or more lengthy incisions and the dividing of the sternum; by contrast, using the system 100, the operator may be able to perform the CABG procedure through the much less invasive subxiphoid incision 404.

Referring to FIGS. 5A-7B and continuing with the example of a CABG procedure, in various embodiments the system 100 can help facilitate performance of a CABG procedure at different locations on the surface of the heart 102. Referring to FIGS. 5A and 5B, the support body 110 is positioned to perform a CABG procedure on an anterior surface 501 of the heart 102. A positioning device 505 may be inserted through the same subxiphoid incision 404 through which the support body 110 is inserted into the body. The positioning device 505 may be used to lift or otherwise position the heart 102 and hold it in place while the CABG procedure is performed. The positioning device 505 may be situated with the aid of the optical system 315 on the support body 110 (FIG. 3). The handle 311 may be manipulated by the user to direct the support body 110 to a desired location on the heart 102. Surgical tools, such as an endoscopic scalpel 591 and a manipulating tool 593, such as a probe or forceps, may be used in connection with the system 100 to complete the procedure, as described further below.

Referring to FIGS. 6A and 6B, in various embodiments the support body 110 is positioned on a lateral surface 601 of the heart 102. As compared to the situation depicted in FIGS. 5A and 5B, performing a procedure on the lateral surface 610 of the heart 102 may not involve moving the heart using a positioning device 505 (FIG. 5A). However, various embodiments of the support body 110 permit rotation of the eversion mechanism 120 and the stabilizer 122 relative to the support body 110 to facilitate disposing the eversion mechanism 120 and the stabilizer 122 on the lateral surface 601 of the heart 102. Referring to FIGS. 7A and 7B, the support body 110 also may be positioned on an inferior surface 701 of the heart 102. Performing a CABG procedure on the interior surface 710 of the heart 102 may not necessitate rotation of the eversion mechanism 120 and the stabilizer 122 or use of a positioning device 505. The handle 311 may be manipulated by the user to direct the support body 110 to a desired location on the heart 102.

Referring to FIG. 8, in various embodiments the CABG procedure proceeds with securing the eversion mechanism 120 and the stabilizer 122 in place on the heart 102 followed by making an incision in the receiving passage 104. To proceed with the CABG procedure, the eversion mechanism 120 is situated directly over the receiving passage 104 that is to receive the graft, such as from a saphenous vein or other donor passage (not shown in FIG. 8). The stabilizer 122 is then secured to the surface of the heart 102 to hold the eversion mechanism 120 in place. The stabilizer 122 may be connected to a vacuum source (not shown) so that openings in an underside of the stabilizer 122 may grip the heart 102 to hold the stabilizer 122 and, in turn, the eversion mechanism 120 in place on the heart 102. Alternatively, the stabilizer 122 may include mechanical grips, such as prongs, to anchor the stabilizer 120 to the heart 102. Once the eversion mechanism 120 is thus secured in place, a clamp or suture may be applied to the receiving passage 104 ahead of the location where the eversion mechanism 120 has been positioned (where "ahead" is used to denote the clamp or suture being situated to block the blood flow to the portion of the receiving passage 104 where the eversion mechanism 120 is situated). Alternatively, blood flow may be stopped by the application of a tourniquet or another technique of applying direct external pressure to the receiving passage 104.

After the blood flow has been stopped, the opening 207 is formed in the receiving passage 104 within the area bounded by the eversion mechanism 801. The opening 207 may be formed by, for example, making an incision in the receiving passage 104, such as by using an endoscopic scalpel 591. The endoscopic scalpel 591 or other cutting tool (not shown) may be inserted through the same subxiphoid incision 404 through which the support body 110 was inserted. The formation of the opening 207, such as by using the endoscopic scalpel 591, may be guided by the optical system 315 (FIG. 3) on the support body 110.

Referring to FIG. 9A and in various embodiments, after the incision is made to form the opening 207, the eversion mechanism 120 is used to evert the edges 205 of the opening 207 to prepare the receiving passage 104 to receive the saphenous vein or other donor passage (not shown in FIG. 9A). As previously described, in various embodiments, the eversion mechanism 120 uses suction to engage the edges 205 of the opening 207 and draw the edges 205 to a rim 910 of the eversion mechanism 120. For example, suction may be applied from a vacuum source (not shown) outside the body and conveyed through the support body 110 to the eversion mechanism 120 through a conduit (not shown) that extends through the handle 311 and is applied through openings 916 (FIG. 9B) in the rim 910. The suction may be applied to the rim 910 via conduits 912 extending between the stabilizer 122 and the rim 910. The manipulating tool 593 (not shown in FIG. 9A) may be used to push or prod the edges 205 toward the rim 910 to aid the suction applied through the rim 910 in taking hold of the edges 205 around the opening 207.

Referring to FIG. 9B, external sides 911 of the edges 205 around the opening 207 are drawn toward the openings 916 in the rim 910 of the eversion mechanism 120. Holding the edges 205 around the opening in place forms the receiving flange 204, of which internal surfaces 913 of the edges 205 face outward to receive the donor flange 206 (FIG. 2).

Referring to FIG. 10A and in various embodiments, after the receiving flange 204 is presented by the eversion mechanism 120, the donor support mechanism 130 is used to position the donor passage 106, such as a saphenous vein. With the eversion mechanism 120 and the stabilizer 122 in place over the receiving passage 104 on the heart 102 and the eversion mechanism 120 forming the receiving flange, as previously described the donor passage 106 is positioned on the donor support mechanism 106. Because the donor passage 106 is removable (and has been harvested from another location in the patient's body to perform the CABG procedure), the donor passage 106 may be manually positioned on an end 1010 of the donor support mechanism 130.

Referring to FIG. 10B, the donor passage 106 is secured to the end 1010 of the donor support mechanism 130. At an opening in an end 211 of the donor passage 106, the edges 209 of the opening in an end 211 of the donor passage 106 are drawn back over the end 1010 of the donor support mechanism 130 to form the donor flange 206. The donor flange 206 presents internal surfaces 1013 of the edges 211 of the donor passage 106 face outward to engage the receiving flange 204. Once the donor flange 206 of the donor passage 106 is sutured to the receiving flange 204 of the receiving passage 104, as described below, the donor support mechanism 130 is removed from the donor passage 106.

Referring again to FIG. 10A, in various embodiments the donor support mechanism 106 includes two segments 1031 and 1033 that meet at a joint 1032. The two segments 1031 and 1033 are held together when the donor passage 106 is inserted into the donor support mechanism 130 and the edges 209 of the opening in an end 211 of the donor passage 106 are drawn back over the end 1010 of the donor support mechanism 130 to form the donor flange 206. After the donor passage 106 is sutured to the receiving passage 104, the segments 1031 and 1033 are removed from one another at the joint 1032 and removed from around the donor passage 106. Thus, the donor support mechanism 130 is removable after the CABG procedure, leaving the sutured donor passage 106 in place.

Referring to FIGS. 11A and 11B, in various embodiments the donor support mechanism 130 is moved into place over the eversion mechanism 120 to perform the CABG procedure. Referring to FIG. 11A, the donor support mechanism 130 supports the donor passage 106 to prepare for the anastomosis procedure, but the donor support mechanism is not yet in place over the eversion mechanism 120. Referring to FIG. 11B, the donor support mechanism 130 is moved into place over the eversion mechanism 120 where the donor passage 106 is sutured to the receiving passage 104 to complete the CABG procedure.

Referring to FIG. 12, in various embodiments the opposing guide sections 210 of the suturing mechanism 200 are positioned on the eversion mechanism 120 and the donor support mechanism and are disposed around the passage juncture 212 (as also shown in FIG. 2). More specifically, the receiving guide section 222 is mounted on or is integrally formed as part of the rim 910 of the eversion mechanism 120. The donor guide section 223 is mounted on or is integrally formed with the end 1010 of the donor support mechanism 130. Thus, when the donor support mechanism 130 (to which the donor passage 106 is secured to form the donor flange 206) is moved into place over the eversion mechanism 120 (to which the receiving passage 104 is secured to form the receiving flange 204), the passage junction 212 is formed and is already received between the receiving guide section 222 and the donor guide section 223. As a result, the helical channel 240 surrounds the passage junction 212. With the helical channel 240 in place around the passage junction 212, the needle 280 is motivated through the helical channel 240 to suture the passage junction 212 and secure the graft.

Referring to FIGS. 13A and 13B, in various embodiments the needle 280 includes a flexible needle 280 configured to conform to the helical channel 240. Referring to FIG. 13A, the needle 280 may have a straight shape in an undeformed position. A pointed leading end 1392 is configured to pierce the tissue of the receiving passage 104 and the donor passage 106 as the needle 280 moves through the helical channel 140. A trailing end 1394 is coupled with or configured to be attached to a filament 290. Referring to FIG. 13B, when motivated through the helical channel 240 (not shown in FIG. 13B), the needle 280 may curve to assume a helical shape 1390 to conform to the shape of the helical channel 240. The needle 280 is thus able to direct the filament 290 through the helical channel 240. Moving the needle 280 and the filament 290 through the helical channel 240 sutures the receiving passage 104 and the donor passage 106 to complete the grafting procedure.

Referring to FIG. 14, in various embodiments an illustrative method 1400 of performing an anastomosis procedure is provided. The method 1400 starts at a block 1405. At a block 1410, at a first opening in a side of a receiving passage, a first edge of the first opening is everted around a periphery of the first opening to form a receiving flange that presents a first interior face. At a block 1420, a donor passage is provided that has an end that terminates in a second opening. At a block 1430, a second edge of the second opening is everted to form a donor flange that presents a second interior face. At a block 1440, the second interior face of the donor passage is positioned adjacent the first interior face of the receiving passage to form a passage juncture. At a block 1450, a filament is motivated along a helical path around the passage juncture to suture the second interior face of the donor passage to the first interior face of the receiving passage. The method 1400 ends at a block 1445, with the passage juncture sutured together to complete the grafting of the donor passage and the receiving passage.

It will be appreciated that the detailed description set forth above is merely illustrative in nature and variations that do not depart from the gist and/or spirit of the claimed subject matter are intended to be within the scope of the claims. Such variations are not to be regarded as a departure from the spirit and scope of the claimed subject matter.

What is claimed is:

1. An apparatus comprising:
    an eversion mechanism configured to engage a first external surface of a receiving passage adjacent a first opening in the receiving passage in order to create a receiving flange presenting a first interior face;
    a donor support mechanism configured to support a donor passage with an opening in an end in an everted position that forms a donor flange presenting a second interior face, and further configured to present the second interior face of the donor flange against the first interior face of the receiving flange to present a passage juncture;
    a first opposing guide section configured to be disposed along a first exterior surface of the receiving flange;
    a second opposing guide section configured to be disposed along a second exterior surface of the donor flange, wherein opposing interior surfaces of the first and second opposing guide sections define a helical channel; and
    a suturing mechanism configured to motivate a filament through the helical channel around the passage juncture to suture the second interior face of the donor passage to the first interior face of the receiving passage.

2. The apparatus of claim 1, wherein the eversion mechanism includes a first suction device configured to apply suction to the first external surface of the receiving passage adjacent the first opening in order to create the receiving flange that presents the first interior face.

3. The apparatus of claim 1, wherein the first opposing guide section is configured to be operably coupled with the eversion mechanism and the second opposing guide section is configured to be operably coupled with the donor support mechanism.

4. The apparatus of claim 1, further comprising a flexible needle configured to receive an end of a suture and further configured to conform to the helical channel.

5. The apparatus of claim 1, further comprising a stabilizer configured to support the first suturing apparatus against a body passage adjacent a first opening formed in a side of a receiving passage.

6. The apparatus of claim 1, wherein the first opposing guide section is integrally formed with the eversion mechanism and the second opposing guide section is integrally formed with the donor support mechanism.

7. A system comprising:
a support body configured to be inserted into a body;
a camera system operably coupled with the support body, wherein the camera system is enabled to convey imaging data from the support body to an operator;
an eversion mechanism that extends from the support body and that is configured to engage a first external surface of a receiving passage adjacent a first opening in the receiving passage in order to create a receiving flange presenting a first interior face;
a donor support mechanism that extends from the support body and that is configured to support a donor passage with an opening in an end in an everted position that forms a donor flange presenting a second interior face, and further configured to present the second interior face of the donor flange against the first interior face of the receiving flange to present a passage juncture;
a first opposing guide section configured to be disposed along a first exterior surface of the receiving flange;
a second opposing guide section configured to be disposed along a second exterior surface of the donor flange, wherein opposing interior surfaces of the first and second opposing guide sections define a helical channel; and
a suturing mechanism configured to motivate a filament through the helical channel around the passage juncture to suture the second interior face of the donor passage to the first interior face of the receiving passage.

8. The system of claim 7, wherein the eversion mechanism includes a first suction device configured to apply suction to the first external surface of the receiving passage adjacent the first opening in order to create the receiving flange that presents the first interior face.

9. The system of claim 7, wherein the suturing mechanism includes a flexible needle configured to receive an end of the filament and to move the filament through the helical channel.

10. The system of claim 7, wherein the first opposing guide section is integrally formed with the eversion mechanism and the second opposing guide section is integrally formed with the donor support mechanism.

* * * * *